(12) United States Patent
Schulman

(10) Patent No.: US 7,524,679 B2
(45) Date of Patent: Apr. 28, 2009

(54) METHODS FOR CULTURING HUMAN LUNG MAST CELLS AND USES THEREOF

(75) Inventor: Edward S. Schulman, Philadelphia, PA (US)

(73) Assignee: Philadelphia, Health and Education Corporation, Philadelphia, PA (US)

( * ) Notice: Subject to any disclaimer, the term of this patent is extended or adjusted under 35 U.S.C. 154(b) by 349 days.

(21) Appl. No.: 10/344,493

(22) PCT Filed: Aug. 8, 2001

(86) PCT No.: PCT/US01/25033

§ 371 (c)(1),
(2), (4) Date: Jun. 20, 2003

(87) PCT Pub. No.: WO02/12448

PCT Pub. Date: Feb. 14, 2002

(65) Prior Publication Data

US 2004/0014208 A1    Jan. 22, 2004

(51) Int. Cl.
*C12N 5/00* (2006.01)
(52) U.S. Cl. .................. 435/377; 435/325; 435/375
(58) Field of Classification Search .......... 435/373, 435/383, 384, 386
See application file for complete search history.

(56) References Cited

U.S. PATENT DOCUMENTS 6,255,107 B1 * 7/2001 Kawai et al. ............. 435/326

OTHER PUBLICATIONS

Valent et al., "Induction of differentiation of human mast cells from bone marrow and peripheral blood mononuclear cells by recombinant human stem cell factor/kit ligand in long term culture", Blood, vol. 80, No. 9, Nov. 1, 1992 : pp. 2237-2245.*
Okayama et al., "Human lung mast cells are enriched in the capacity to produce granulocyte macrophage colony stimulating factor in response to IgE dependent stimulation", Eur J Immunol., 1998, 28:708-715.*
Oskeritzian et al., "Recombinant Human (rh) IL-4-Mediated Apoptosis and Recombinant Human IL-6-Mediated Protection of Recombinant Human Stem Cell Factor-Dependent Human Mast Cells Derived from Cord Blood Mononuclear Cell Progenitors[1]", Journal of Immunology 1999 163 :5105-5115 XP-002279520.
Schulman et al., "ATP Modulates Anti-IgE-Induced Release of Histamine from Human Lung Mast Cells", Am. J. Respir. Cell Mol. Biol. 1999 20:530-537 XP-002279521.
Schulman et al., "Long-term Cultivation of Human Lung Mast Cells", J. Allergy Clin. Immunol. 2001 107 (2) :S288 XP009030686.
Dvorak et al., "Human Mast Cells Use Conservation and Condensation Mechanisms During Recovery from Degranulation", Laboratory Investigation 1986 54 (6) :663-678.
Dvorak et al., "Human Mast Cells Synthesize New Granules During Recovery from Degranulation. In Vitro Studies With Mast Cells Purified From Human Lungs", Blood 1988 71 (1) :76-85.
Schulman et al., "Human Lung Mast Cells : Purification and Characterization", Journal of Immunology 1982 129 (6) :2662-2667.
Valent et al., "Induction of Differentiation of Human Mast Cells From Bone Marrow and Peripheral Blood Mononuclear Cells by Recombinant Human Stem Cell Factor/Kit-Ligand in Long-Term Culture", Blood 1992 80 (9) :2237-2245.

* cited by examiner

*Primary Examiner*—Lora E Barnhart
(74) *Attorney, Agent, or Firm*—Licata & Tyrrell P.C.

(57) ABSTRACT

Methods for culturing human lung mast cells in the absence of co-culture with feeder cells which are viable for longer than 4 days are provided. Also provided are methods for using these human lung mast cell cultures to assess biological and pharmacological activities of these cells in vivo and to identify modulators of the survival, proliferation, function and phenotypic expression of human lung mast cells. Modulators identified via these cells are useful in the prevention and treatment of diseases involving human lung mast cell function.

1 Claim, No Drawings

METHODS FOR CULTURING HUMAN LUNG MAST CELLS AND USES THEREOF

BACKGROUND OF THE INVENTION

Allergic responses to commonly encountered substances in the everyday environment, or hypersensitivity reactions, are commonplace, with millions of Americans suffering from some form of hypersensitivity. Such allergic reactions are also often associated with the existence of asthma, a common disorder of the airways that is estimated to affect 4 to 5 percent of the population of the United States. There are no known cures for allergies or asthma, and currently available treatments in most cases only alleviate symptoms.

The human lung mast cell is a critical effector of respiratory hypersensitivity responses characteristic of both allergies and asthma. The release of inflammatory mediators from lung mast cells plays a central role in the pathophysiology of human allergic disorders. However, attempts to study the biochemistry and pharmacology of human lung mast cells has been stymied by technical difficulties in purification, low yields, inconsistent responsiveness to IgE-mediated stimulation, and short survival in vitro of these cells.

Methods to purify human lung mast cells are extremely difficult to execute and only a few laboratories worldwide have been successful at providing purified preparations of these cells.

Schulman et al. (J. Immunol. 1982 129:2662-2667) describe a method for purification of human lung mast cells where human lung tissue is finely minced and then dispersed into a single cell suspension using a series of enzymes. However, the cells purified by this method remain viable in culture for only short-term (24-96 hours).

Attempts have been made to co-culture human lung mast cells with fibroblasts and human tumor cell lines to extend the time period during which they are viable. Human lung mast cells cultured in culture dishes coated with human fibroblasts survived for approximately 15-30 days during which time the mast cells did not purify and did not proliferate (Levi-Schaffer et al. J. Immunol. 1987 139(2):494-500; and Dvorak et al. Am. J. Pathol. 1991 139(6):1309-18) while human lung mast cells cultured in dishes coated with a human tumor line survived for approximately 30 days (Hartzell et al. ARRD 139 (4):A119, 1989). The precise mechanisms and chemical effectors through which the feeder cells allowed prolonged survival of mast cells was not determined in any of these studies.

Also, it is not known whether human lung mast cells in these co-cultures remain fully differentiated and maintain their unique characteristics manifested in vivo. Specifically, it is not known whether the critical cellular processes associated with mediator synthesis, storage and release remain unaltered under these culture conditions and thus maintain their specific phenotype as human lung mast cells. It is known that these mast cells do not proliferate under these conditions.

Attempts have also been made to raise mast cells from CD34 positive precursor stem cells. Most commonly, the source of these cells is human fetal cord blood, but peripheral blood and fetal liver have also been used. The ability to grow mast cells followed the cloning, in the early 1990's of stem-cell factor. Key to the success was combining stem cell factor with specific cytokine growth factors; usually interleukin-6 and/or Interleukin-3 surprisingly, addition to this mast cell culture system of interleukin-4, the cytokine that most defines allergic immunity, induces programmed cell death (apoptosis)(Oskeritzian et al. J. Immunol. 1999 162:5105-5115). Thus, the combination of growth factors mandatory for cultivating precursor-derived mast cells is critical. Although mast cells obtained by this method appeared to be useful for studies of areas such as mast cell biochemistry and signal transduction, their comparability to human lung mast cells was not conclusively demonstrated. Some reports have questioned the full maturity of such cells, with up to 50% of the nuclei in these cells displaying atypia which may be indicative of aberrant development (Bischoff et al. Proc. Natl. Acad. Sci. USA 1999 96:8080-8085; Dvorak et al. J. Leukoc. Biol. 1993 54:465-485; Toru et al. J. Allergy & Clin. Immunol. 1998 102:491-502). Furthermore, these cells and mature human lung mast cells responded differently to several physiologic and pharmacologic agonists. For example, human cord blood-derived mast cells can produce IL-13 only under co-stimulation with anti-IgE and stem cell factor, whereas human lung mast cells require only anti-IgE to produce IL-13. The cells also exhibit disparate responses to adenosine. Adenosine inhibits IgE-mediated histamine release in cord-blood precursor-derived mast cells as opposed to enhancement of anti-IgE-induced release observed in freshly isolated human lung mast cells(Kanbe et al. Int. Arch. Allergy Immunol. 1999 119(2):138-142; Suzuki et al. Biochem. Biophy. Res. Commun. 1998 242:697-702; Peachell et al. Am. Rev. Respir. Dis. 1988 138(5):1143-1151).

Bischoff et al. (Proc. Natl. Acad. Sci. USA 1999 96:8080-8085) described enzymatic dispersion methods for intestinal mast cell purification from human intestinal surgery specimens. However, fundamental differences in the biology of mast cells originating in different tissues and organs of the human body have been well documented. For example, basic differences in triggers, surface receptors and mediators released from skin mast cells versus lung mast cells are remarkable. These major differences render it impossible to directly apply methods for culturing viable mast cells derived from one organ such as the intestine to the culturing of mast cells from another organ such as the lung (Schulman, E. S. and D. G. Raible. 1998. In: *Pulmonary Diseases and Disorders*, vol. 1, $3^{rd}$ edition, A. P. Fishman (ed.), McGraw Hill: New York, pp. 289-301; Schulman, E. S. Crit. Rev. Immunol. 1993 13:35-70).

SUMMARY OF THE INVENTION

An object of the present invention is to provide a method for producing human lung mast cell cultures which comprises partially purifying human lung mast cells from human lung tissue and culturing the partially purified human lung mast cells in a culture medium that includes growth factors, preferably cytokine growth factors such as stem cell factor, and in the absence of co-culture with feeder cells. In a preferred embodiment, the human lung mast cells are also cultured in the presence of interleukin-4. Viable human lung mast cells can be maintained from these cultures for more than 4 days. Further, this method can be used to obtain a pure, homogeneous population or human lung mast cells.

Another object of the present invention is to provide methods for using these human lung mast cell cultures in vitro to determine pharmacological and biochemical activities of human lung mast cells in vivo.

Another object of the present invention is to provide methods for screening for modulators of human lung mast cells which comprises contacting the purified, human lung mast cell cultures with a test compound and assessing the ability of the test compound to modulate the biology of human lung mast cells. These methods can be used to identify modulators of human lung mast cell survival, proliferation, function and/or phenotypic expression. Modulators identified in accordance with these methods may be useful in prevention and/or treatment of diseases involving lung mast cell function. Such diseases include, but are not limited to, allergic hypersensitivity, asthma, chronic obstructive lung disease, local inflammatory processes such as state post myocardial infarction and fibrosing lung disorders.

DETAILED DESCRIPTION OF THE INVENTION

Methods have now been developed that allow for long-term culture of human lung mast cells in the absence of co-culture with feeder cells. Further, the methods of the present invention can be used to obtain pure, homogenous populations of human lung mast cells. The cells produced in accordance with the methods of the present invention are not only maintained in a viable condition for months but also maintain a capacity to divide and proliferate. Further, these cultured mast cells maintain phenotypic expression of human lung mast cells in vivo, thus retaining responsiveness to various stimulants and membrane receptor-mediated agents as well as demonstrating both biochemical and pharmacological activities characteristic of human lung mast cells in vivo.

In the context of the present invention, by "long-term" culture of cells it is meant a culture of human lung mast cells not co-cultured with feeder cells which remains viable for more than 4 days. In a preferred embodiment, long term cultures of the present invention remain viable at least for several weeks to several months.

In the context of the present invention by "purified" or "pure" cells it is meant a population of cells that comprises at least 80%, and more preferably at least 95%, human lung mast cells.

In the method of the present invention, human lung mast cells are partially purified to at least 15% from normal human lung tissue. The partially purified human lung mast cells are then cultured in medium supplemented with growth factors. In a preferred embodiment, the medium is supplemented with cytokine growth factors such as stem cell factor. More preferably, the medium is supplemented with both stem cell factor and interleukin-4. Additional growth factors which can be included in the medium of these cultures can be routinely determined by one skill in the art in accordance with the teachings provided herein.

In a preferred embodiment of the present invention, the partially purified human lung mast cells are obtained as follows. Grossly normal human lung tissue is finely minced and thoroughly washed in divalent cation free Tyrode=s buffer made from sterile water at 22EC containing 100 µg/ml gentamycin, 100 µg/ml streptomycin, 100 U/ml penicillin, and 0.5 µg/ml amphotericin. Tissues and cells are kept in antibiotics at all steps. Release buffers are tested with the E-toxate assay (Sigma Chemical Co., St. Louis, Mo.) to confirm that they were free of significant endotoxin. Minced fragments are then enzymatically dispersed into a single cell suspension by two incubations with the enzymes pronase (2 mg/ml) and chymopapain (0.5 mg/ml) followed by two similar incubations in with collagenase (1 mg/ml) and elastase Type I (10 U/ml). Liberated cells are then thoroughly washed and cultured overnight in RPMI-1640 with antibiotics and the mast cells are partially purified with counter-current elutriation.

However, as will be understood by those of skill in the art upon reading this disclosure, other methods for partially purifying human lung mast cells for use in the culture methods of the present invention can also be used. For example, Okayama et al. describe a method for purifying human lung mast cells by affinity magnetic selection with monoclonal antibody YB5.B8 against c-kit (purity>90%) (J. Immunol. 1995 155, 1796-1808).

The partially purified human lung mast cells are then cultured in medium supplemented with growth factors. In a preferred embodiment, the cells are cultured in 96 well plates in a medium supplemented with cytokine growth factors such as stem cell factor. A preferred concentration of stem cell factor is 25 ng/ml. More preferred is supplementation of the medium with stem cell factor and interleukin-4. A referred concentration of stem cell factor in this embodiment is also 25 ng/ml while a preferred concentration of interleukin-4 is 10 ng/ml. Most preferred is culturing of the cells in a humidified atmosphere containing approximately 5% carbon dioxide at 37° C. at an initial density in culture medium such as RPMI 1640 also containing 10% fetal calf serum, 25 mM HEPES pH 7.4, 2 mM L-glutamine, 100 µg/ml penicillin, 100 µg/ml gentamycin sulfate, 100 µg/ml streptomycin, and 0.5 µg/ml amphotericin B further supplemented with stem cell factor. Overnight, the cells settle to the bottom of the wells. Cultured lung mast cells of the present invention are preferably renourished 3 times each week, exchanging the upper one-half of the culture medium with new medium containing the cytokines at the same concentrations originally added to that well. During culture, remaining non mast cells die off and purity of the human lung mast cells continues to increase.

For example, at culture inception, human lung mast cells from 7 individual lungs at purities ranging from 13% to 85% were placed at an initial density of 0.4 H $10^6$/ml in culture medium supplemented with stem cell factor (25 ng/ml) and interleukin-4 (10 ng/ml) in a humidified atmosphere containing 5% $CO_2$ at 37° C. All mast cells fractions placed in culture had undergone elutriation. Within the first week of culture about 50% of the human lung mast cells died off. However, within 4 weeks, human lung mast cell numbers equaled or exceeded the number of mast cells at culture inception. In addition, contaminating non-mastocytes died off and purity continued to increase. Within 4-6 weeks, cultures appeared homogeneous as determined by staining with toluidine blue and with the mast cell-specific stain tryptase; chymase enzyme positivity was 10±4.7% (range 0-19.9%, n=4) of the cells, similar to that found in freshly isolated human lung mast cells. The intensities of staining with toluidine blue, tryptase and chymase were also comparable to that seen in freshly isolated human lung mast cells. Preparations of 80% starting purity or better, reached apparent homogeneity within 2-4 weeks. However, even preparations of mast cells with 13-25% purity post elutriation and Percoll density separation, reached apparent homogeneity (~100% purity) within 6-8 weeks.

In contrast, in eight preparations in which elutriation was omitted and mast cells were partially purified (to 5-20%) from enzymatically dispersed lung cells using Percoll alone, the mast cell survived, but so did cellular contaminating cells. Thus, none of the eight preparations reached homogeneity; instead purities of mast cells ranged from 10-48%. Accordingly, partial purification of human lung mast cells via elutriation prior to culturing in growth factors such as stem cell factor is preferred to obtain the purified human lung mast cell cultures of the present invention.

Proliferative, phenotypic and functional characteristics of human lung mast cell cultures of the present invention were assessed.

Proliferation of the human lung mast cells was demonstrated in experiments wherein cell count was first determined in each well at weeks 5 through 8. Approximately one-half of the cells was then removed from each well. Cell counts were repeated one week later and it was found that human lung mast cell numbers increased by 60±3% (mean ±SEM, n=8).

In addition, it was confirmed experimentally that this proliferation is from the original tissue mast cells themselves, and not scarce CD34(+) precursors. It has been suggested that mast cells arise from CD34+ bone marrow precursors that enter the circulation in a cloaked form, and then arrive in tissues where they differentiate in a manner dictated by the local microenvironment (Oskeritzian, C. A. and Schwartz, L. B. Human mast cells and basophils: heterogeneity and mediators: In Asthma and Rhinitis. Busse WW and Holgate St, eds. $2^{nd}$ edition. pp. 275-295, Blackwell Science, London, 2000). Recently, CD34(+) cells have been described in the airways of atopic asthmatics and atopic nonasthmatic subjects, suggesting that inflammatory cells may differentiate within the lung (Robinson et al. Am. J. Respir. Crit. Care Med. 1999 20:9-13). Therefore, flow cytometry was used to evaluate within 1-2 weeks of culture inception, the percentage of cells that were CD34(+). In three individual preparations, CD34+ cells constituted only 1-2% of total cells, thus confirming that the human lung mast cells and not the precursor cells were proliferating.

Uptake of $^3$H-thymidine was also monitored as a measure of survival and proliferation of human lung mast cell cultures of the present invention in the presence of different cytokine growth factors. In these experiments, $^3$H-thymidine was added to human lung mast cell aliquots from three individuals at 5 through 7 weeks of culture. Human lung mast cells cultured in medium with interleukin-4, added in the absence of stem cell factor, produced no proliferation in excess of that seen in culture medium alone. In the absence of stem cell factor, cells died within 3-5 days. Medium with stem cell factor alone produced a 60% increase in uptake. Medium to which stem cell factor and interleukin-4 were added produced a greater than 4-fold increase in proliferation versus stem cell factor alone. Other cytokine growth factors such as interleukin-9, when added to the cultures medium containing stem cell factor and interleukin-4, produced an even greater enhancement in proliferation. In contrast, interferon-γ added to culture medium containing stem cell factor and interleukin-4 produced a marked reduction in proliferation of these cells.

Uptake of BrdU was also monitored to assess cell division. At day 0, BrdU (10 µM) was added to human lung mast cells cultured in culture medium containing stem cell factor (25 ng/ml) and interleukin-4 (10 ng/ml). Weekly, aliquots were removed for analyses. By 3-4 weeks of culture inception, a high percentage of positively stained cells was noted (73.0±5.9%, n=3), thus indicating that the majority of human lung mast cells, and not a sparse subset entered cell division.

Histamine is considered the most prominent preformed mediator of the mast cell. Therefore, cultured human lung mast cells of the present invention were examined during culture weeks 5 through 7 for histamine content. Histamine content per mast cell was 3.18±0.43 pg/cell (range 0.69-6.68 pg/cell, mean ±SEM, n=19). This compares favorably to the histamine content of 3.6±0.5 pg reported for freshly isolated human lung mast cells (Schulman et al. J. Immunol. 1982 129:2662-67).

Release of histamine in response to various stimuli was also examined. Spontaneous histamine release in all preparations was <1% (n=22). However, dose-dependent histamine release was observed in cultures of the present invention exposed to the antibody 22E7. Furthermore, the release exceeded that found in freshly isolated human lung mast cells at culture inception (release 0-15%). Specifically, all preparations (n=22) demonstrated robust histamine release responses at a maximum stimulatory concentration of antibody (1:10,000 dilution); maximum release ranged between 17%-80%. Substance P and compound 48/80, which are effective secretagogues in rodent (Sullivan et al. Am. J. Pathol. 1976 85(2):437-64; and Irman-Florjanc, T. and Erjavec, F. Agents Actions 1983 13(2-3):138-41) and in human mast cells from skin, synovium and heart but not lung (Lawrence et al. J. Immunol. 1987 139(9):3062-9; de Paulis et al. Arthritis Rheum,. 199639(7):1222-33; Patella et al. Int. Arch. Allergy Immunol. 1995 106(4):386-93; Ennis, M. Agents Actions 1982 12(1-2):60-3), failed to provoke histamine release from the cultured human lung mast cells of the present invention, indicating a functional phenotype comparable to that of freshly isolated human lung mast cells.

The effects of extracellular ATP upon enhancement of IgE-mediated stimulation was also examined in the human lung mast cell cultures of the present invention. In four experiments with these cell cultures, the effects of ATP (10-4 M) on release provoked by submaximal IgE cross-linkage with the monoclonal antibody 22E7 were examined. 22E7 alone caused 17.9±8.2% histamine release. In the presence of ATP, 22E7-induced release was enhanced to 39.5±12.2%. Similar enhancement was shown for uridine 5' triphosphate (UTP), indicating that cell surface P2Y receptors mediated these responses. As previously found for freshly isolated human lung mast cells, neither ATP nor UTP alone triggered appreciable histamine release.

Beta-receptor responsiveness of human lung mast cell cultures of the present invention were also examined using the prototype agonist, isoproterenol, as well as with the long-acting beta agonist, salmeterol. Both agents produced a profound inhibition of histamine release in the subnanomolar range ($IC_{50}=9\times10^{-11}$M and $10^{-10}$M for isoproterenol and salmeterol, respectively).

Human lung mast cell cultures of the present invention also responded to the non-immune stimulus calcium ionophore A23187 in similar fashion to freshly isolated human lung mast cells.

These data indicate that the human lung mast cell cultures of the present invention are pure and viable in culture for periods of weeks or months, rather than only days. In addition, the majority of cells in cultures of the present invention not only survive for months but also proliferate. Within 2 to 6 weeks, the cells cultured by the method of the present invention become virtually homogeneous (approaching 100% purity). Furthermore, these cells in culture demonstrate the ability to respond to the immune reaction by the release of histamine and as well as non-immune stimulus such as the calcium ionophore A23187, as do freshly isolated human lung mast cells.

Accordingly, the present invention provides a method for producing large amounts of human lung mast cells that are viable and functional for periods as long as several months. The method involves culturing partially purified human lung mast cells from either intact tissues or from dispersed cell solutions with growth factors, preferably cytokine growth factors such as stem cell factor, more preferably stem cell factor and interleukin-4. These cells in culture survive long-term, proliferate, and remain functional as human lung mast cells.

The present invention also relates to methods for use of these human lung mast cell cultures in biological and/or pharmacological assays to better understand human lung mast cell functions. Examples of mast cell functions which can be studied with these cell cultures include, but are not limited to, histamine content, histamine release, allergic and non-allergic challenge, and mediator release, and the effects thereupon of pharmacologic agents, including products of arachidonic acid metabolism and cellular proteins. The cell cultures of the present invention can also be used in assays monitoring factors affecting survival and proliferation of human lung mast cells.

These assays can also be used to identify modulators of human lung mast cell function. Methods for screening for modulators of human lung mast cells comprise contacting the purified, human lung mast cell cultures of the present invention with a modulator and assessing the ability of the modulator to alter the survival, proliferation, function and/or phenotypic expression of human lung mast cells. By "modulator" it is meant to be inclusive of test compounds such as small inorganic molecules or proteins or fragments thereof, pharmacologic agents or biological compounds, as well as environmental conditions, such as changes in oxygen levels, humidity levels, etc., which either increase or decrease survival, proliferation, function and/or phenotypic expression of human lung mast cells. Assays for assessing survival, proliferation, function and/or phenotypic expression of human lung mast cells can be performed in accordance with teachings provided herein. Modulators identified in accordance with these methods may be useful in prevention and/or treatment of diseases involving lung mast cell function. Such diseases include, but are not limited to, allergic hypersensitivity, asthma, chronic obstructive lung disease, or fibrosing lung disorder.

The following nonlimiting examples are provided to further illustrate the present invention.

EXAMPLES

Example 1

Materials

The following were purchased: DNase, pronase (Calbiochem, San Diego, Cailf.), collagenase (Worthington, Freehold, N.J.); and gelatin (Difco Laboratories, Detroit, Mich.). Porcine elastase Type I, chymopapain, substance P, adenosine, ATP and UTP (Sigma Chemical Co., St. Louis, Mo.). The monoclonal anti-FcεRI antibody 22E7 was obtained from Hoffman La Roche (Nutley, N.J.).

Example 2

Buffers

Lung fragments were washed with Tyrode's buffer containing (g/l); NaCl, 8.0; KCl, 0.2; $NaH_2PO_4$, 0.05, and glucose, 1.0. The buffer was titrated to pH 7.2 by the addition of $NaHCO_3$. Mast cell isolation and elutriation were performed in TGMD: Tyrode's buffer with (g/l) gelatin (1.0), magnesium (0.25; 1 mM), and DNase (0.01), added. PAGCM was a Pipes-albumin (0.003%) buffer containing (g/l): glucose (1.0), $CaCl_2.2H_2O$, 0.14 (1 mM); and $MgCl_2.6H_2O$, 0.2 (1 mM). All buffers were filtered through 0.22 micron filters, then stored and maintained under sterile conditions. Water and buffers were routinely tested (E-toxate, Sigma) to confirm absence of detectable endotoxin.

Example 3

Human Lung Mast Cell Purification

Grossly normal human lung tissue freshly derived from thoracotomy specimens was finely minced and then extensively washed free of blood and alveolar cells using divalent cation-free Tyrode's buffer. Fragments were twice incubated in a mixture of Pronase (2 mg/ml) and chymopapain (0.5 mg/ml). Freed cells were harvested through NYTEX nylon cloth (150 microns pore size). Residual fragments were twice further exposed to a mixture of collagenase (1 mg/ml) and elastase (10 units/ml). All incubations and washes were performed at 37° C.; recovered cells were immediately washed three times in large volumes of TGMD. Resultant lung cell suspensions contained mast cells purities ranging from 1-8% as determined by alcian blue staining (Gilbert et al. Blood 1975 46(2):279-86). Human lung mast cells were further separated from cellular contaminants by counter-current elutriation (Schulman et al. J. Immunol. 1983 131:1936-41). In some experiments, elutriation was followed by flotation of human lung mast cell-enriched fractions through discontinuous Percoll gradients prior to culture (Ishizaka et al. J. Immunol. 1983 130:2357-62).

Example 4

Human Lung Mast Cell Culture

Following isolation and enrichment procedures described Example 3, approximately $10^7$ human lung mast cells were cultured in a humidified atmosphere containing 5% $Co_2$ at 37° C. at an initial density of $0.4 \times 10^6$/ml in culture medium (RPMI 1640, 10% FCS, 25 mM HEPES pH 7.4, 2 mM L-glutamine, 100 μg/ml penicillin, 100 μg/ml streptomycin, 100 μg/ml gentamycin sulfate, and 0.5 μg/ml amphotericin B, further supplemented with stem cell factor (25 ng/ml)±interleukin-4 (10 ng/ml), using multiwell plates. Overnight, cells settled to the bottom of the wells. Cells were renourished once to thrice weekly, exchanging the upper one-half of the culture medium with new medium containing the original concentration of growth factors. Counts were performed twice weekly using the alcian blue technique to determine human lung mast cell recovery and purity. For photodocumentation, cytocentrifuge preparations on slides were stained with toluidine blue and other cytochemical stains.

Example 5

Histamine Release Assay

Mast cells ($10\text{-}50 \times 10^3$/tube) in PAGCM were preincubated at 37° C. then challenged with buffer or anti-FcεRI in doubling dilutions. In experiments examining the effects of beta-agonist and purinergic agonists, agents were added to cells at 37° C. for 15 minutes prior to FcεRI-mediated challenge. Twenty minutes following challenge, cells were rapidly pelleted and supernatants removed for histamine analysis. Histamine release was expressed as the net histamine released divided by the total histamine content ×100%. The total cellular histamine content was determined following cell lysis with 2% perchloric acid. Spontaneous histamine release was always <2% of cellular histamine and generally <1%. Histamine measurements were performed using the automated spectrofluorometric method of Technicon (Tarrytown, N.Y.). Variations between replicates were consistently <5%. All assays were run in duplicates.

Example 6

RNA Extraction and PCR

Total cellular RNA (tcRNA) was isolated from cultured human lung mast cells using a modified phenol-chloroform extraction technique adapted from Chomczynski and Sacchi (Anal. Biochem. 1987 162:156-159). Likewise, for positive controls, whole blood was processed by Ficoll-Hypaque gradient centrifugation to obtain peripheral blood mononuclear cells and cells similarly treated for tcRNA (Jaffe et al. Am. J. Respir. Cell Mol. Biol. 1995 13:665-75). Purified mast cell tcRNA was treated with 10 units Heparinase-I (Sigma Co., St. Louis, Mo.) at room temperature for 2 hours to neutralize the inhibitory effects of mast cell heparin on RT-PCR reactions. cDNA was synthesized from 1 mg tcRNA using oligo(dT) primers and the murine Moloney leukemia virus reverse transcriptase (Life Technologies, Inc., Grand Island, N.Y.) at 37° C. for 1 hour in the presence of 20 units RNasin with 10 nM each of deoxynucleotide triphosphate (Promega Corporation, Madison, Wis.).

Product-specific primers used in the PCR step for GAPDH, IL-5 and IL-13 primers have been previously published (Jaffe et al. Am. J. Respir. Cell Mol. Biol. 1995 13:665-75; Jaffe et al. Am. J. Respir. Cell Mol. Biol. 1996 15:473-81).

PCR was performed using 1 unit Taq DNA polymerase (Life Technologies, Inc., Grand Island, N.Y.) for 30 cycles (30 seconds at 94° C., 30 seconds at 60° C., 60 seconds at 72° C.) followed by an additional product extension step (72° C. for 5 minutes) using a programmable thermal cycler (GeneAmp 9600, Perkin Elmer, Foster City, Calif.). PCR products were separated using agarose gel electrophoresis and visualized by ethidium bromide staining using a digital image analysis system (Gel Doc 1000, Bio-Rad Laboratories, Hercules, Calif.).

Example 7

Tryptase and Chymase Immunocytochemistry

Cultured cells were assessed in cytocentrifuge preparations fixed in Carnoy's fixative for 30 minutes and washed in $dH_2O$, washed in balanced salt solution for 30 minutes, drained and placed in blocking solution for 60 minutes at room temperature. Immunocytochemistry was performed using a primary antibody against human tryptase at 1:100 dilution (alkaline phosphatase labeled IgG1) and an antibody against human chymase 1:300 dilution (biotin labeled, IgG1) (Chemicon, Temecula, Calif.). Appropriate mouse IgG1 controls were used. After washing cells ×3 in balanced salt solution (BSS), for chymase staining, extra-avidin alkaline phosphatase at a 1:10,000 dilution was added overnight in a moist chamber. After rinsing in BSS ×3 for 20 minutes, substrate (Vector red) was added and allowed to develop in the dark for 45 minutes. At least 500 cells/slide were counted.

Example 8

Proliferation Assays Using $^3$H-thymidine

At days 35-49, when cultures contained >95-99% mast cells, $2\times10^4$ mast cells in 50 µl culture medium were placed in triplicate in 96 well flat-bottomed plates and $^3$H-thymidine (0.5 µCi/50 µl/well) added. After four days, cells were harvested on a glass fiber filter, washed ×3, and radioactive uptake was evaluated by a beta counter. Since the cultures contained virtually homogeneous populations, the counts reflected mast cell proliferation and not that of cellular contaminants. The results were expressed as the percent increase in radioactivity over mast cell cultured in medium alone.

Example 9

Proliferation Assays Using Bromodeoxyuridine (BrdU)

The percentage of cells positive for this marker reflected the actual percentage of mast cells having undergone mitosis. BrdU (10 µM) was added at culture inception and aliquots removed at the intervals indicated in results. Following cytocentrifugation, slides were fixed, permeabilized in 0.07N NaOH for 2 minutes, and then incubated in FITC-conjugated anti-BrdU Ab (α-BrdU) from Becton Dickinson (San Jose, Calif.) for 30 minutes. Slides were then stained with 0.04 µg/ml propidium iodide to delineate all cells. The FITC-conjugated α-BrdU mAb allowed enumeration of BrdU-positive cells under the fluorescence microscope.

What is claimed is:

1. A method of producing homogeneous human lung mast cell cultures comprising:

partially purifying by elutriation human lung mast cells to at least 13% from human lung tissue; and culturing the partially purified human lung mast cells in the presence of stem cell factor or stem cell factor and interleukin-4 and the absence of interleukin-6 for more than 4 days, wherein the human lung mast cells remain viable for at least several weeks, wherein the human lung mast cells maintain a capacity to divide and proliferate, and wherein proliferation of said mast cells is increased when cultured in the presence of stem cell factor and interleukin-4 as compared to proliferation of human lung mast cells cultured in medium with interleukin-4 added in the absence of stem cell factor and as compared to proliferation of human lung mast cells cultured in medium with stem cell factor added in the absence of interleukin-4.

* * * * *